United States Patent [19]

Hunsucker

[11] 4,049,819
[45] Sept. 20, 1977

[54] METHOD OF COMBATTING MICROORGANISMS EMPLOYING SUBSTITUTED OXAZOLINES

[75] Inventor: Jerry H. Hunsucker, Terre Haute, Ind.

[73] Assignee: IMC Chemical Group, Inc., Terre Haute, Ind.

[21] Appl. No.: 656,486

[22] Filed: Feb. 9, 1976

[51] Int. Cl.² .................... A01N 9/22; A01N 9/28
[52] U.S. Cl. .......................... 424/272; 71/67; 106/210; 252/8.5 R
[58] Field of Search .......................... 424/272

[56] References Cited

U.S. PATENT DOCUMENTS

| | | | |
|---|---|---|---|
| 3,336,145 | 8/1967 | Purcell | 106/176 |
| 3,509,260 | 4/1970 | Wehrmeister | 424/272 |
| 3,523,123 | 8/1970 | Wehrmeister | 260/307 |
| 3,652,513 | 3/1972 | Gayliardi | 260/80.3 |
| 3,769,293 | 10/1973 | Hetzel et al. | 260/307 F |

*Primary Examiner*—Allen J. Robinson
*Attorney, Agent, or Firm*—Robert H. Dewey; Howard E. Post

[57] ABSTRACT

A method of combatting microorganisms by applying to them or to their habitat an oxazoline represented by the formula

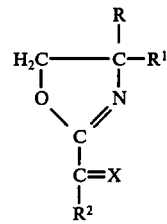

where R and R¹ can be methyl, ethyl or hydroxymethyl and can be the same or different; X is $H_2$ or $(-CH_2OH)_2$ and R² is alkyl of 4 to 16 carbon atoms.

9 Claims, No Drawings

METHOD OF COMBATTING MICROORGANISMS EMPLOYING SUBSTITUTED OXAZOLINES

BACKGROUND OF THE INVENTION

This invention relates to a method of combatting microorganisms. In a particular aspect, this invention relates to a method of combatting microorganisms by the use of a member of the class of substituted oxazolines.

H. L. Wehrmeister, in U.S. Pat. No. 3,509,260 disclosed that oxazolines wherein X in the formula below is $H_2$ and $R^2$ is the terminally unsaturated decene radical were effective bactericides and fungicides. Such compounds have many advantages. They contain no halogens and are of a very low order of toxicity to warm-blooded animals; they readily hydrolyze with rupture of the ring in the presence of an acid, so such compounds are non-persistent. Because of these properties they do not constitute a threat to the user nor to wildlife that might encounter them. There is however a continuing need for additional anti-microbials, especially those of the oxazoline class.

SUMMARY OF THE INVENTION

It is an object of this invention to provide a method of combatting microorganisms.

It is another object of this invention to provide a method of combatting microorganisms using a substituted oxazoline.

Other objects of this invention will be apparent to those skilled in the art from the disclosure herein.

It is the discovery of this invention to provide a method of combatting microorganisms by applying to them or to their habitat an oxazoline represented by the formula

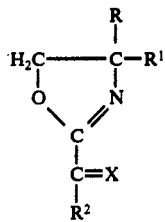

where R and $R^1$ can be methyl, ethyl or hydroxymethyl and can be the same or different, X is $H_2$ or $(-CH_2OH)_2$ and $R^2$ is an alkyl group of 4 to 16 carbon atoms.

DETAILED DISCUSSION

The compounds used in the practice of this invention are known in the art. Compounds wherein X is $(-CH_2OH)_2$ were disclosed by H. L. Wehrmeister in U.S. Pat. No. 3,523,123, which is incorporated herein by reference. Compounds wherein X is $H_2$ are old in the art. A good description for their preparation is described by R. F. Purcell in U.S. Pat. No. 3,336,145, which is also incorporated herein by reference.

The oxazoline preferred for the practice of this invention depends to a considerable degree on the particular organism to be combatted, since there is a surprising degree of selectivity. Generally, however, those oxazolines wherein X is $(-CH_2OH)_2$, R and $R^1$ are each $-CH_2OH$ and $R^2$ is alkyl of from 8 to 14 carbon atoms are broad spectrum anti-microbials. However those wherein X is $(-CH_2OH)_2$, R and $R^1$ are each $CH_3$ and $R^2$ is 10 or 12 are also very effective. When X is $H_2$ and R and $R^1$ are methyl, the compound wherein $R^2$ is alkyl of 10 carbon atoms is also a preferred oxazoline.

The preferred oxazolines accordingly include but are not limited to:

2-[1,1-bis(hydroxymethyl)undecyl]-4,4-dimethyl-2-oxazoline

2-[1,1-bis(hydroxymethyl)tridecyl]-4,4-dimethyl-2-oxazoline

2-[1,1-bis(hydroxymethyl)nonyl]-4,4-bis(hydroxymethyl-2-oxazoline

2-[1,1-bis(hydroxymethyl)undecyl]-4,4-bis(hydroxymethyl-2-oxazoline

2-[1,1-bis(hydroxymethyl)tridecyl]-4,4-bis(hydroxymethyl)-2-oxazoline

2[1,1-bis(hydroxymethyl)pentadecyl]-4,4-bis(hydroxymethyl)-2-oxazoline.

2-undecyl-4,4-dimethyl-2-oxazoline.

The compounds useful in the practice of this invention are generally effective to combat the growth of bacteria or fungi at low concentrations, e.g. 10 ppm. There is of course no upper limit to the amount that can be used but generally they become uneconomical above about 5000 ppm and accordingly a use concentration of 10-5000 ppm is contemplated. Generally, however, a concentration between 100 and 2000 ppm is preferred and a concentration of 500-1000 ppm is particularly preferred.

Most of the oxazolines wherein X is $(-CH_2OH)_2$ are conveniently applied to the environment inhabited by microorganisms as an aqueous solution or dispersion. They are particularly effective in aqueous systems such as starch adhesives and solutions, drilling muds for the petroleum industry and in water-dilutable cutting oils based on petroleum hydrocarbons.

These oxazolines, especially those wherein X is $H_2$, are also soluble in, e.g., alcohols, ketones and most other organic solvents, including hydrocarbons. Solutions of the water-insoluble oxazolines in such solvents can be used in substantially non-aqueous or 2-phase systems when desired.

The method of combatting microoganisms of this invention comprises application of the anti-microbial oxazolines of this invention to a substratum infested with the microorganisms to be combatted or to a substratum to be protected from infestation with the microorganisms. The term substratum as used herein is intended to mean the environment or medium upon which an organism grows and includes both animate and inanimate matter, such as animal and vegetable, living or dead, and the soil. The term microorganisms as used herein is intended to include bacteria and fungi but not algae, viruses, protozoa, etc. The term anti-microbial as used herein is intended to include the terms bactericidal, bacteriostatic, fungicidal and fungistatic. No attempt has been made to determine if the products actually cause the death of the organism or merely prevent their growth.

The anti-microbial oxazolines of this invention can be used without dilution for the control of a wide variety of organisms. Preferably, however, they are used in a dispersed form in a suitable extending agent.

The term "dispersed" is used herein in the widest possible sense. When the anti-microbial agents of this invention are said to be dispersed, it can mean that the particles of the anti-microbial agents are molecular in the form of a true solution in a suitable organic solvent.

It can also mean that the particles are colloidal in size and distributed throughout a liquid phase in the form of particles held in suspension by wetting agents. The term also includes particles which are distributed in a semisolid viscous carrier such as petrolatum or soap or other ointment base in which they may be actually dissolved in the semi-solid or held in suspension in the semisoliol with the aid of suitable wetting or emulsifying agents. The term "dispersed" also means that the particles may be mixed with and distributed throughout a solid carrier providing a mixture in particulate form, e.g. pellets, granules, powders, or dusts. The term "dispersed" also includes mixtures which are suitable for use as aerosols including solutions, suspensions, or emulsions of the anti-microbial oxazolines of this invention in a carrier such as the chlorofluoroalkanes which boil below room temperature at atmospheric pressure.

The term "extending agent" as used herein includes any and all of those substances in which the anti-microbial oxazolines of this invention are dispersed. It includes, therefore, the solvents of a true solution, the liquid phase of suspensions, emulsions or aerosols, the semisolid carrier of ointments and the solid phase of particulate solids, e.g. pellets, granules, dusts and powders.

Usually it is preferred to supply these oxazolines as a concentrate such as a spray base or a wettable powder, i.e., a particulate solid base in such form that it can be easily mixed with water or a solid extender (e.g. powdered clay or talc) or other low-cost material available at the point of use. In such a concentrate, the oxazoline generally will be present in a concentration of 5 to 95 percent by weight. The remainder can be any one or more of the well-known adjuvants, such as a surface active agent (e.g. a detergent, soap, or other emulsifying or wetting agent) clays, solvents diluents, carrier media, adhesives, spreading agents, humectants, and the like.

When the anti-microbial oxazolines of this invention are to be used in the form of aerosols, it is convenient to dissolve them in a suitable solvent and disperse the resulting solution in the aerosol propellant, i.e., dimethyl ether, propane, dichlorodifluoromethane or other chlorofluoroalkane.

The anti-microbial oxazolines of this invention are preferably supplied to the microorganisms or to their environment in the form of emulsions or suspensions. Emulsions or suspensions are prepared by dispersing one or more of the oxazolines of this invention in water with the aid of a surface active agent. The anti-microbial oxazolines can be emulsified directly or they can first be dissolved in an organic solvent and then emulsified. The term "surface active agent" includes the various "emulsifying agents", "dispersing agent", "wetting agents" and "spreading agents" that can be mixed with the oxazolines of this invention in order to obtain a dispersion of the oxazolines in water. These surface active agents include the well-known anionic, cationic, or non-ionic surface active agents. In general, the water-soluble non-ionic surface active agents are preferred.

The anti-microbial oxazolines of this invention can be dispersed by suitable methods (e.g., tumbling or grinding) in solid extending agents and supplied to the organisms' environment in particulate form. Solid extending agents include both inorganic and organic materials. Inorganic materials include tricalcium phosphate, calcium carbonate, kaolin, bole, kieselguhr, talc, bentonite, fuller's earth, pyrophillite diatomaceous earth, calcined magnesia, volcanic ash, sulfur and the like. Organic materials include powdered cork, powdered wood, and powdered nut shells. The preferred solid extending agents are the adsorbent clays, e.g., bentonite. These mixtures can be used for anti-microbial purposes in the dry form, or by addition of water-soluble surface active agents the dry particulate solids can be rendered wettable by water so as to obtain stable aqueous dispersions or suspensions suitable for use as sprays.

For some purposes the anti-microbial oxazolines of this invention can be advantageously dispersed in a semi-solid extending agent such as petrolatum or soap (e.g., the sodium salt of a fatty acid) with or without the aid of solubility promoters and/or surface active agents.

The dispersions described above can be used as such in combatting microorganisms or they can be formulated in a concentrated form suitable for mixing with other extending agents. A useful concentrate is a mixture of one or more anti-microbial oxazolines of this invention with a water-soluble surface active agent in the weight proportions of 0.1 to 15 parts of surface active agent with sufficient of the anti-microbial oxazoline of this invention to make 100 parts by weight. Such a concentrate can be readily made into a spray for combatting microorganisms by diluting with water. An example of such a concentrate is a mixture of 95 parts by weight of oxazoline and 5 parts by weight of water-soluble non-ionic surface active agent such as polyoxyethylene derivative of sorbitan monolaurate.

Another useful concentrate which can be readily made into a spray for combatting microorganisms is a solution (preferably as concentrated as possible) of one or more anti-microbial oxazolines of this invention in an organic solvent therefor, to form a liquid concentrate. Preferably a minor amount (e.g., 0.5 to 10 percent by weight of the weight of the oxazoline) of a water-soluble surface active agent is also dissolved therein. An example of such a concentrate is a solution of oxazoline in acetone containing a water-polyoxyethylene glycol non-ionic surface active agent and a water-soluble alkylaryl sulfonate anionic surface active agent.

The preferred surface active agents which can be employed in preparing the emulsifiable, wettable or dispersible compositions of this invention include the anionic and non-ionic surface active agents. The preferred anionic surface active agents are the well-known water-soluble alkali metal alkylaryl sulfonates, e.g., sodium dodecylbenzene sulfonate. The preferred non-ionic surface active agents are the water-soluble polyoxyethylene derivatives of the mono-higher fatty acid esters of hexitol anhydrides such as mannitan or sorbitan.

In contolling or combatting microorganisms the oxazolines of this invention are supplied to the organisms or to their environment in a lethal or toxic amount. This can be done by dispersing one or more of the oxazolines or a composition containing it, in, on or over an environment or substratum infested with, or to be protected from, the microorganisms. The oxazoline or composition containing it can be dispersed in any conventional method which permits contact between the organisms and the anti-microbial agents of this invention. Conventional methods include power dusters, boom and hand sprayers, and spray dusters. For subsurface application to the soil such dispersing can be carried out by simply mixing the oxazoline as is or compositions containing one or more of them with the soil or by applying a liquid solution of the oxazoline to accomplish subsurface penetration and impregnation therein.

The invention will be better understood with reference to the following examples. The examples are intended only to illustrate the invention and it is not intended that the invention be limited thereby.

EXAMPLE 1

2-Pentyl-4,4-bis(hydroxymethyl)-2-oxazoline was prepared by reacting caproic acid with 2-amino-2-methyl-1-propanol according to the method of Purcell, U.S. Pat. No. 3,336,145. This product was then condensed with formaldehyde in a 1:2 mole ratio, respectively, according to the method of Wehrmeister, U.S. Pat. No. 3,523,123. There was obtained 2-[1,1-bis(hydroxymethyl)butyl]-4,4-bis(hydroxymethyl)-2-oxazoline. It was tested for anti-bacterial and anti-fungal activity against nine bacteria (4 Gram positive and 5 Gram negative) and eight fungi (6 molds and 2 yeasts). These organisms are listed in Table 1 wherein each of them is assigned a number which identifies it in Table 3. Results are reported as minimum inhibitory concentration, which is the range between the highest concentration which permits growth and the lowest concentration which prevents growth. These ranges are listed in Table 2. They increase exponentially and each range is identified by an alphabetical letter from A to H. Because of uncontrollable variables, such as the vigor of the organism, the data are reproducible to about plus or minus one range. The results obtained by the use of the oxazoline of this example and of examples 2–12 are given in Table 3. The results show that the oxazoline of example 1 is effective in combatting at least some organisms in concentrations as low as 250 ppm.

Table 1

| ORGANISMS | IDENTIFYING NUMBER IN TABLE 3 |
|---|---|
| Bacteria | |
|    Bacillus subtilis | 1 |
|    Staphylococcus aureus | 2 |
|    Streptococcus faecalis | 3 |
|    Sarcina lutea | 4 |
|    Escherichia coli | 5 |
|    Aerobacter aerogenes | 6 |
|    Pseudomonas aeruginosa | 7 |
|    Salmonella typhii | 8 |
|    Desulfovibrio aestaurii | 9 |
| Fungi | |
|    Cladosphorium herbarum | 10 |
|    Cephalosporium species | 11 |
|    Trichophyton mentagrophytes | 12 |
|    Aspergillus niger | 13 |
|    Aureobasidium pullulans | 14 |
|    Fusarium moniliforme | 15 |
|    Sacchromyces cerevisiae | 16 |
|    Candida albicans | 17 |

Table 2

| MINIMUM INHIBITORY RANGE, ppm | INDENTIFIED IN TABLE 3 AS |
|---|---|
| <33 | A |
| 33–65 | B |
| 65–125 | C |
| 125–250 | D |
| 250–500 | E |
| 500–1000 | F |
| 1000–2000 | G |
| >2000 | H |

EXAMPLES 2–12

The experiment of example 1 was repeated in all essential details except that various oxazolines were substituted for the oxazoline of example 1. The oxazolines are represented by the formula in Table 4 and the substituents R, $R^1$ and $R^2$ are identified. In Table 4 are listed the lowest concentration of oxazoline which prevented growth of at least one organism.

Table 3

Inhibitory Properties of Oxazolines $$\underset{\underset{R^2}{|}}{\overset{R}{\underset{H_2C}{\overset{|}{C}}-\overset{N}{\underset{O}{\diagdown}}\overset{R^1}{\diagup}}}C(-CH_2OH)_2$$

Activity Range Against Microorganism

| Ex. No. | Oxazoline R | R¹ | R² | Bacteria 1 | 2 | 3 | 4 | 5 | 6 | 7 | 8 | 9 | 10 | 11 | 12 | Fungi 13 | 14 | 15 | 16 | 17 |
|---|---|---|---|---|---|---|---|---|---|---|---|---|---|---|---|---|---|---|---|---|
| 1 | $CH_3$ | $CH_3$ | $C_4H_9$ | F | F | G | F | F | D | F | F | D | G | E | D | G | G | — | D | H |
| 2 | $CH_3$ | $CH_3$ | $C_8H_{17}$ | F | E | E | E | F | — | F | F | E | D | B | — | E | F | F | B | E |
| 3 | $CH_3$ | $CH_3$ | $C_{10}H_{21}$ | A | A | A | A | F | B | G | F | E | D | A | D | F | G | — | A | H |
| 4 | $CH_3$ | $CH_3$ | $C_{12}H_{25}$ | C | C | D | A | G | A | F | G | A | G | A | E | G | F | H | A | H |
| 5 | $CH_3$ | $CH_3$ | $C_{14}H_{29}$ | G | F | G | E | G | D | G | F | F | F | D | E | F | F | G | E | H |
| 5A | $CH_3$ | $CH_3$ | $C_{16}H_{33}$ | G | G | F | E | E | F | G | G | G | G | F | D | G | G | F | D | H |
| 6 | $CH_2OH$ | $CH_2OH$ | $C_4H_9$ | F | F | F | C | E | — | F | E | C | F | E | D | F | F | — | D | H |
| 7 | $CH_2OH$ | $CH_2OH$ | $C_6H_{13}$ | D | D | $C^2$ | $A^2$ | $F^2$ | E | $F$-G | $F^2$ | D | E | $B^2$ | D | $E^2$ | $E^2$ | C | — | G |
| 8 | $CH_2OH$ | $CH_2OH$ | $C_8H_{17}$ | A | A-C | C | A | F | $A^2$ | G | E | $E^2$ | B-C | A | B | E | D | E | A-C | E-F |
| 9 | $CH_2OH$ | $CH_2OH$ | $C_{10}H_{21}$ | A | B | A-B | A | G-H | B-D | H | F-G | D | C | $A^2$ | B-C | F-G | F-H | D | $A^2$ | B |
| 10 | $CH_2OH$ | $CH_2OH$ | $C_{12}H_{25}$ | A-B | A-D | A | $A^2$ | F | — | H | H | F | D-E | B | D-E | G | H | H | A | $H^2$ |
| 11 | $CH_2OH$ | $CH_2OH$ | $C_{14}H_{29}$ | A-B | A | A | A | G-H | B-D | H | H | F | F | $A^2$ | — | F-G | F-H | G | $A^2$ | B |
| 12 | $CH_2OH$ | $CH_2OH$ | $C_{16}H_{33}$ | G | G | B | A | H | C | H | H | D | E | B | D | H | G | A | C | H |

*The superscript signifies duplicate results.

Table 4

| OXOZOLINE OF EXAMPLE NO. | CONCENTRATION PREVENTING GROWTH OF AT LEAST ONE ORGAnISM, PPM |
| --- | --- |
| 2 | 65 |
| 3 | <33 |
| 4 | <33 |
| 5 | 250 |
| 5A | 500 |
| 6 | 250 |
| 7 | 65 |
| 8 | <33 |
| 9 | <33 |
| 10 | <33 |
| 11 | <33 |
| 12 | <33 |

EXAMPLE 13-14

The experiment of example 1 was repeated in all essential details except that oxazolines wherein X is $H_2$ were used. THe results, which are given in Table 5, show that the oxazoline of example 13 is effective against several organisms at a concentration less than 33 ppm and the oxazoline of example 14 is effective against at least one organism at a concentration of 65 ppm. The substituents R, $R^1$ and $R^2$ are identified in Table 5.

Table 5

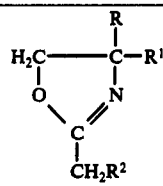

Inhibitory Properties of Oxazolines

| Ex. No. | Oxazoline | | | Activity Range Against Microorganism | | | | | | | | | | | | | | | | |
| --- | --- | --- | --- | --- | --- | --- | --- | --- | --- | --- | --- | --- | --- | --- | --- | --- | --- | --- | --- | --- |
| | | | | Bacteria | | | | | | | | | Fungi | | | | | | | |
| | R | $R^1$ | $R^2$ | 1 | 2 | 3 | 4 | 5 | 6 | 7 | 8 | 9 | 10 | 11 | 12 | 13 | 14 | 15 | 16 | 17 |
| 13 | $CH_3$ | $CH_3$ | $C_{10}H_{21}$ | A | A | A | A | E | B | H | H | E | C | A | A | H | H | — | A | H |
| 14 | $CH_2OH$ | $CH_2OH$ | $C_{12}H_{25}$ | F | F | E | — | H | — | H | H | G | E | C | — | H | H | H | B | H |

EXAMPLES 15-16

The experiment of example 1 is repeated in all essential details except that oxazolines having the following substituents are substituted for the oxazoline of example 1. In each case, X is $(-CH_2OH)_2$.

| Example | R | $R^1$ | $R^2$ |
| --- | --- | --- | --- |
| 15 | $CH_3$ | $CH_2OH$ | $C_{12}H_{25}$ |
| 16 | $C_2H_5$ | $CH_2OH$ | $C_{14}H_{29}$ |
| 17 | H | $C_2H_5$ | $C_{14}H_{29}$ |

The compounds are inhibitory to most microorganisms at a concentration of 1000 ppm.

EXAMPLE 17

A cutting oil emulsion is prepared according to the following formula:

| Light mineral oil | 20 | parts |
| --- | --- | --- |
| Water | 76.5 | |
| Oxazoline of Example 1 | 0.5 | |
| Mixed $C_{18}$ fatty acids | 3 | |
| | 100 | |

The emulsion remains free from microbial contamination when used as a cutting oil.

I claim:

1. A method of combatting bacteria and fungi by applying in an amount lethal to said bacteria and fungi and to the environment inhabitated by them, an oxazoline represented by the formula

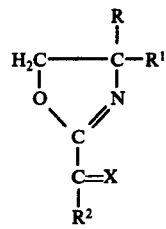

where R and $R^1$ are hydrogen, methyl, or hydroxymethyl and can be the same or different, $R^2$ is an alkyl group of from 4 to 16 carbon atoms and X is $H_2$ or $(-CH_2OH)_2$.

2. The method of claim 1 wherein R and $R^1$ are methyl.

3. The method of claim 1 wherein R and $R^1$ are hydroxymethyl.

4. The method of claim 1 wherein R is hydrogen and $R^1$ is ethyl.

5. The method of claim 1 wherein R is ethyl and $R^1$ is hydroxymethyl.

6. The method of claim 2 wherein X is $(-CH_2OH)_2$.

7. The method of claim 3 wherein X is $(-CH_2OH)_2$.

8. The method of claim 1 wherein X is $H_2$.

9. The method of claim 1 wherein $R^2$ is an alkyl group of from 10 to 16 carbon atoms.

UNITED STATES PATENT AND TRADEMARK OFFICE
CERTIFICATE OF CORRECTION

PATENT NO. : 4,049,819
DATED : September 20, 1977
INVENTOR(S) : Jerry H. Hunsucker It is certified that error appears in the above-identified patent and that said Letters Patent are hereby corrected as shown below:

Column 2, line 11, "ymethyl" should read -- ymethyl) --
Column 2, line 13, "ymethyl" should read -- ymethyl) --
Column 3, line 7, "semisoliol" should read -- semi-solid --
Column 6, Table 2, second column in the heading, "INDENTIFIED" should read -- IDENTIFIED --
Column 7, Table 3 in the formula

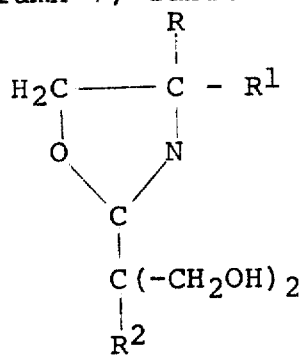   should read   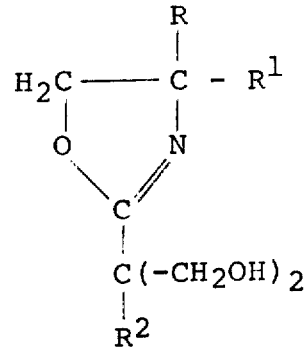

Column 9, Table 4, first column in the heading, "OXOZOLINE" should read -- OXAZOLINE --
Column 9, Table 4, second column in the heading, "ORGAnISM" should read -- ORGANISM --
Column 9, line 19, "THe" should read -- The --

Signed and Sealed this

Thirtieth Day of May 1978

[SEAL]

Attest:

RUTH C. MASON
Attesting Officer

LUTRELLE F. PARKER
Acting Commissioner of Patents and Trademarks